United States Patent [19]

Berg

[11] Patent Number: 4,863,448
[45] Date of Patent: Sep. 5, 1989

[54] POST URINATION DRIP COLLECTOR

[76] Inventor: Skip Berg, P.O. Box 725, Venice, Fla. 34284

[21] Appl. No.: 142,436

[22] Filed: Jan. 11, 1988

[51] Int. Cl.$^4$ ............................................. A61F 5/44
[52] U.S. Cl. .................................... 604/349; 604/352
[58] Field of Search .............. 604/346, 348, 347, 350, 604/351, 352, 353; 128/132 R

[56] References Cited

U.S. PATENT DOCUMENTS

| | | | |
|---|---|---|---|
| 2,448,938 | 9/1948 | Wayne | 604/346 |
| 2,839,060 | 6/1958 | Ormo | 604/352 |
| 2,891,546 | 6/1959 | Galloway . | |
| 3,212,500 | 10/1965 | Bardy . | |
| 3,520,305 | 7/1970 | Davis . | |
| 3,648,700 | 3/1972 | Warner | 604/349 |
| 3,858,584 | 1/1975 | Johnson . | |
| 3,958,574 | 5/1976 | Rohr . | |
| 4,500,314 | 2/1985 | Brendling | 604/349 |
| 4,586,605 | 5/1986 | Newsome | 206/267 |
| 4,589,874 | 5/1986 | Riedel et al. | 206/229 |
| 4,590,931 | 5/1986 | Kidwell | 604/347 |
| 4,601,716 | 7/1986 | Smith | 604/349 |
| 4,627,846 | 12/1986 | Ternstrom . | |
| 4,668,229 | 5/1987 | Fago et al. . | |
| 4,790,835 | 12/1988 | Elias | 604/349 |

FOREIGN PATENT DOCUMENTS

| | | | |
|---|---|---|---|
| 0123661 | 10/1984 | European Pat. Off. | 604/349 |
| 0641521 | 8/1928 | France | 604/349 |
| 2568469 | 2/1986 | France | 604/347 |
| 0329655 | 5/1930 | United Kingdom | 604/349 |

*Primary Examiner*—C. Fred Rosenbaum
*Assistant Examiner*—Mario Costantino
*Attorney, Agent, or Firm*—Charles J. Prescott; Raymond H. Quist

[57] ABSTRACT

A post urination drip collector is formed as a cap having an interior configuration which will mate with the exterior of the glans penis. The drip collector may be sized to receive a larger than normal glans penis to permit the use of one size for all. The drip collector is disposable after one use and is removeably secured by adhesive. The adhesive may be at one location to be adjacent to the neck of the penis and on the top, or it may extend over the entire inner surface of the drip collector. The drip collector may be rolled to a substantially flat circle and packaged in foil or plastic.

12 Claims, 2 Drawing Sheets

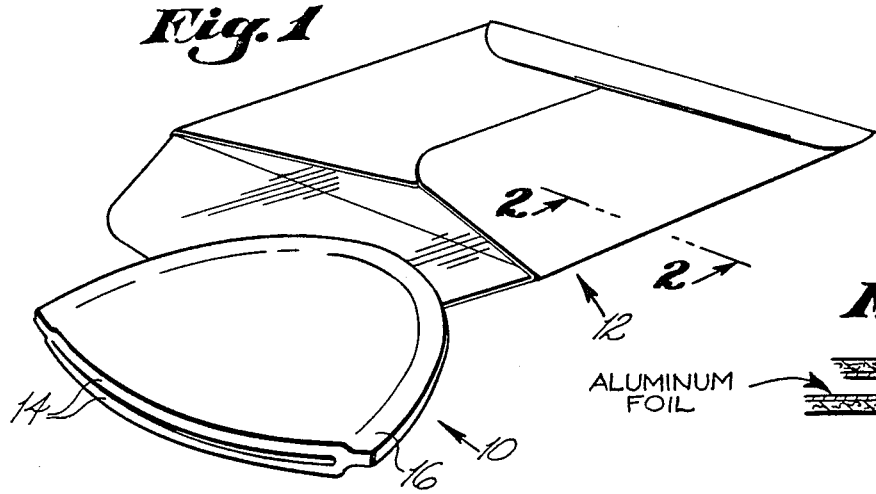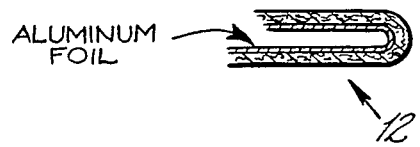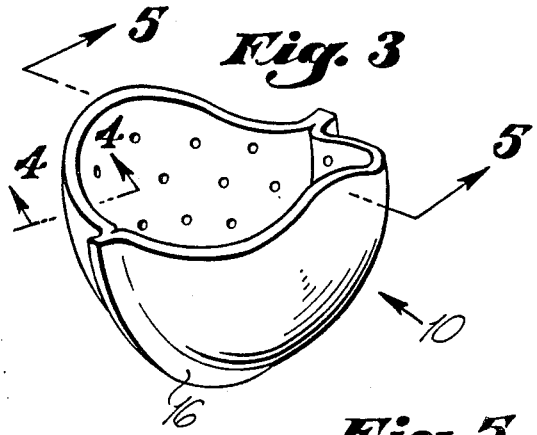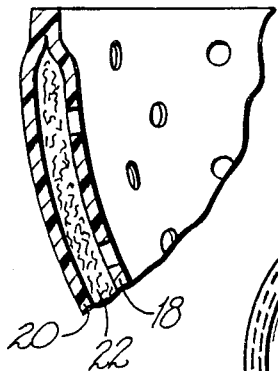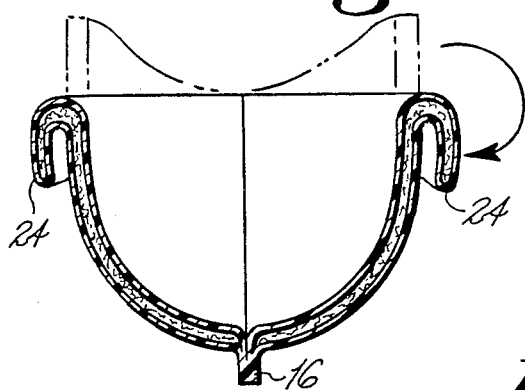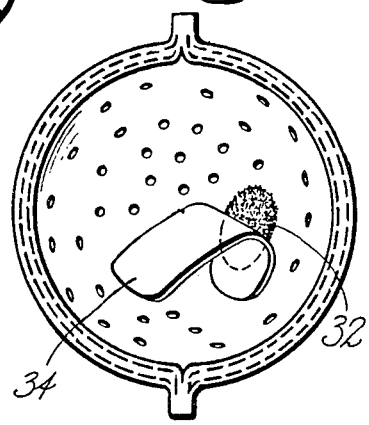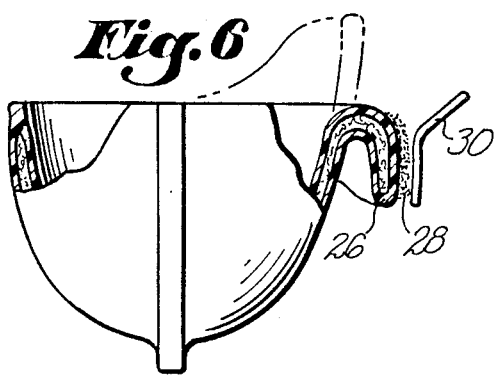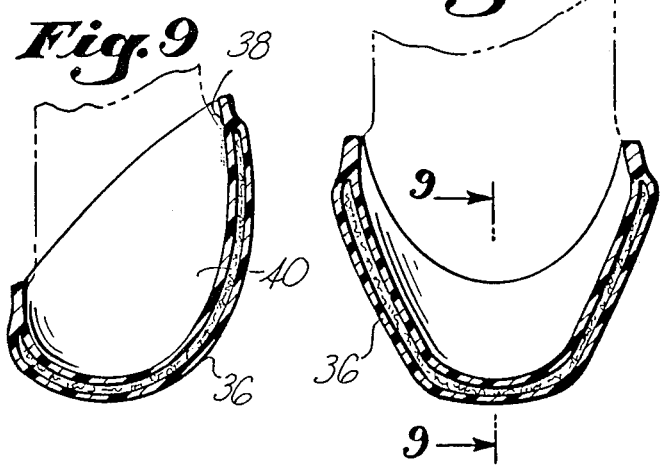

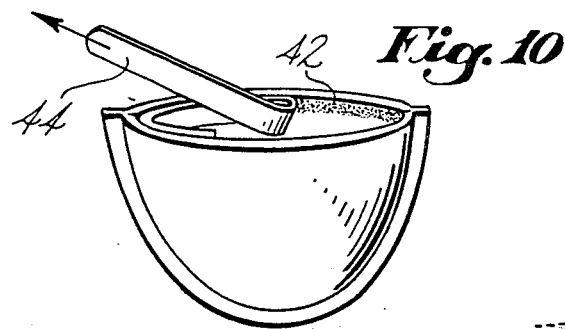
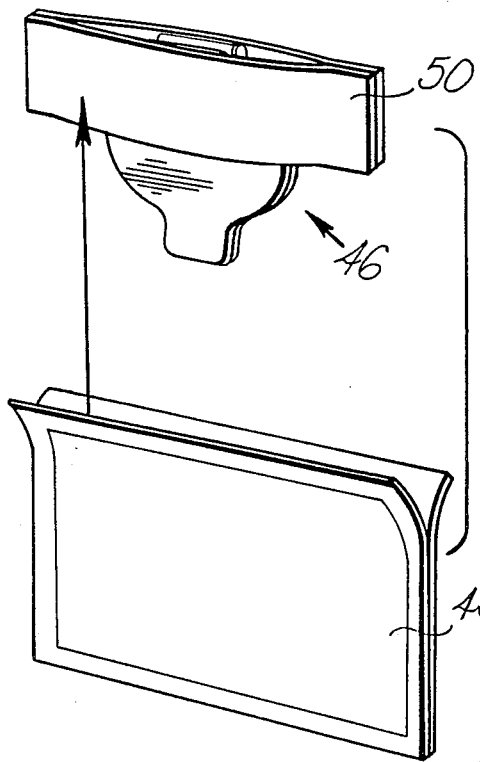
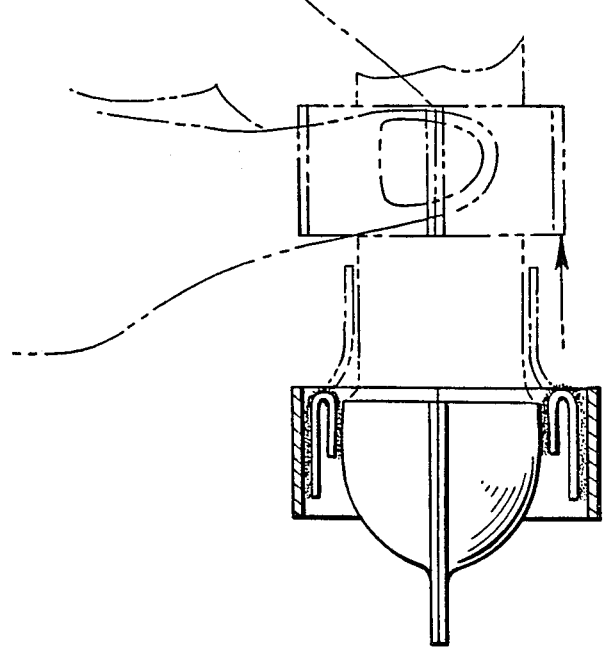
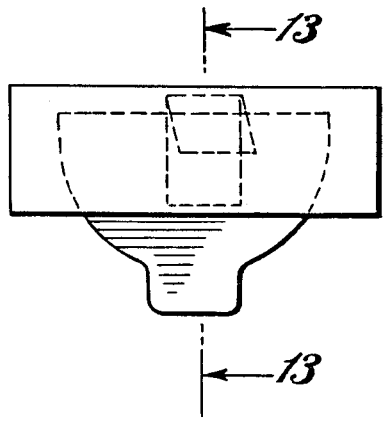
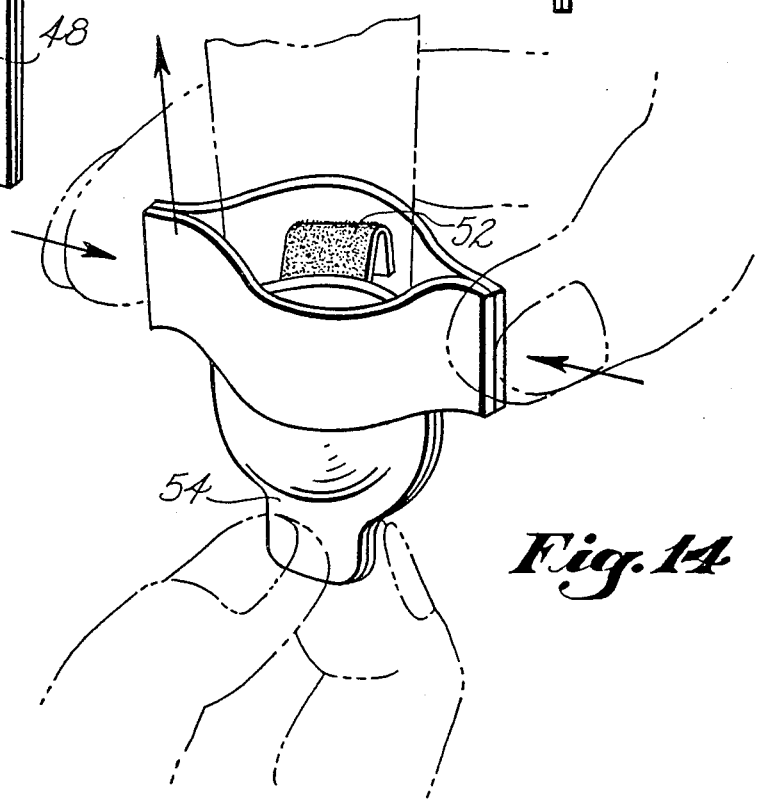

POST URINATION DRIP COLLECTOR

BACKGROUND OF THE INVENTION

1. Field of the Invention

This invention relates to a multilayer cover for the glans penis for the collection and retention of drippage residual after urination or ejaculation.

2. Description of Related Art

After urination, a small amount of urine may remain temporarily in the urethra and drip out some time later. Similarly, after ejaculation, some seminal fluid may subsequently drip from the urethra. This drippage may stain the underwear and even penetrate the trousers. This problem has been previously recognized and various solutions have been proposed.

U.S. Pat. No. 2,891,546, Galloway, entitled: "Male Urethral Fluid-Absorbing Device", discloses an L-shaped adhesive coated sheet with a absorbant L-shaped pad thereon. A small spot of adhesive is exposed to be secured to the under side of the penis behind the head, and the longer arm is wrapped circumferentially about the penis and secured by an uncovered area of adhesive at the end of the arm. The other arm is brought from the bottom forward and folded back along the top of the penis to be secured. This latter arm may be removed during urination and then repositioned.

U.S. Pat. No. 3,212,500, Bardy, entitled: "Hygenic Receptacle for Undergarments", discloses an undergarment with a removable crotch piece in the form of a bag or pocket which may contain a removable pad of absorbent material.

U.S. Pat. No. 3,520,305, Davis, entitled: "Male Urinary Device", discloses a thin sheath joined to a heavier tube for use as a urinal.

U.S. Pat. No. 3,858,584, Johnson, entitled: "Diaper for Male Baby", includes a container for holding a urine absorber as part of a diaper.

U.S. Pat. No. 3,958,574, Rohr, entitled: "Masculine Hygiene Device", discloses a disposable absorbent cup formed of a plurality of plies of paper to cover the end of the penis.

U.S Pat. No. 4,627,846, Ternstrom, entitled: "Incontinence Shield for Men", discloses a multilayer shield which encloses both the penis and the scrotum.

U.S Pat. No. 4,668,229, Fago et al, entitled: "Disposable Absorbent Device for Post-Urinary Drip", discloses a sheath having a urine absorbent disposable lining. The sheath is secured by a loop which will encircle the penis and the scrotum.

U.S Pat. No. 87,932, Hoffman, entitled: "Supporting Bandage", discloses a water-tight bag which contains a sponge. The bag is connected by straps to a bandage secured about the body.

Some of the foregoing patents provide for the collection of greater quantities of fluids than is required for the purposes of the present invention. Others provide structure which is not disposable or is more cumbersome and uncomfortable than is desirable. Not all of the patented arrangements will be equally useful with both circumcized and uncircumcized penis.

It is therefore an object of this invention to provide a post urination drip collector which is disposable after each use.

It is also an object of this invention to provide a post urination drip collector which is small in size so that several can be readily carried and the use of the collector will not cause discomfort.

It is also an object of this invention to provide a post urination drip collector which can be readily packaged for dispensing.

It is also an object of this invention to provide a post urination drip collector which is equally useful for both circumcized and uncircumcized penis.

In accordance with these and other objects, which will become apparent hereafter, the instant invention will now be described with reference to the accompanying drawings.

BRIEF DESCRIPTION OF THE DRAWINGS

FIG. 1 shows diagrammatically a drip collector in accordance with the invention with an associated package;

FIG. 2 is a detail in cross-section taken on the line 2—2 of the package of FIG. 1;

FIG. 3 shows diagrammatically the drip collector of FIG. 1 in an open position;

FIG. 4 is a cross-section showing a detail taken on the line 4—4 of the layer structure of the drip collector of FIG. 3;

FIG. 5 is an elevation in cross-section taken on the line 5—5 of FIG. 3;

FIG. 6 is an elevation showing an alternate structure for the drip collector of FIG. 3;

FIG. 7 is a plan view of the drip collector of FIG. 3;

FIG. 8 is a cross-section of another embodiment of a drip collector in accordance with the invention shown on a phantom penis;

FIG. 9 is a cross-section showing a side view of the drip collector of FIG. 8;

FIG. 10 is a diagrammatic view showing a drip collector with securing adhesive;

FIG. 11 is a diagrammatic view showing another embodiment of a drip collector with an associated package;

FIG. 12 is an elevation of the drip collector of FIG. 11;

FIG. 13 is a cross-section taken on the line 13—13 of FIG. 12 showing the positioning of the drip collector on a phantom penis; and FIG. 14 is a diagrammatic view showing the drip collector being gripped for positioning.

SUMMARY OF THE INVENTION

A post urination drip collector is provided sized to substantially cover only the glans penis of a somewhat larger than normal size. The drip collector is of multilayer construction having an outer liquid impermeable layer, an intermediate liquid absorbent layer and an inner layer which is liquid permeable. The inner surface may have adhesive thereon; which may be a single portion located to be adjacent to the neck of the penis on the upper portion, or which may be applied across the entire inner surface. The adhesive may also be located on strips. The structure may also include aids for placing the drip collector in position. The configuration permits folding of the drip collector to a compact form for packaging.

DETAILED DESCRIPTION OF THE INVENTION

Referring to FIG. 1, post urination drip collector 10 is shown in folded condition adjacent to package 12 in which it is contained for sale or dispensing. Package 12 also provides a convenient way of carrying several of the drip collectors until they are to be used. Package 12, as shown in FIG. 2, may have a lining of aluminum foil to prevent deterioration of the drip collector contained therein. Drip collector 10 has a cap type body, more clearly shown in FIG. 3. The collector may be fabricated in two similar flat halves 14 which are joined at the edge 16 by a heat seal or the like.

As shown in FIG. 4, drip collector 16 is shown to be formed of three layers. Inner layer 18 is a layer of liquid permeable material, outer layer 20 is a layer of liquid impermeable material and intermediate layer 22 is a layer of liquid absorbent material. A closed edge is formed by bonding inner layer 18 and outer layer 20 at seam 24. Layers 18–22 may be the kinds of materials conventionally used in disposable diapers; however, the liquid absorbent material is provided in a thinner layer consonant with the few drops of liquid which are to be absorbed. This thinner layer may not be of uniform thickness, but instead may be thicker adjacent to the urethral opening.

Referring to FIG. 5, the upper edge of drip collector 10 may include oppositely disposed flaps 24 to facilitate holding the drip collector to position it upon the glans penis. Flaps 24 may be folded down from the position shown in broken lines after drip collector 10 is properly positioned. As depicted in FIG. 6, a single flap 26 may be used in lieu of the pair of FIG. 5. Also, the flap(s) may have a portion with adhesive 28 thereon for securing drip collector 10 in place. Adhesive 28 may have removable cover 30 thereon to protect the adhesive until it is to be used.

It is not necessary to have extensive areas of adhesive to hold the drip collector in position. As shown in FIG. 7, a somewhat localized spot 32 may be provided on the inner layer and have cover 34 removeably positioned over it.

FIGS. 8 and 9 show an alternate embodiment 36 of a drip collector having an interior configuration like the exterior of the glans penis. It is shown in position on a phantom penis. The only seam in this configuration is along the top edge. Adhesive 38 is applied in a spot adjacent to the upper edge. Glans penis 40, as depicted, is somewhat larger than the normal glans penis, so that drip collector 36 fits closely. Consequently, the same sized drip collector 36 will fit somewhat loosely on normal or smaller than normal glans penis.

Referring to FIG. 10, adhesive 42 may also be applied in a stripe or band adjacent to the top edge of the drip collector and provided with a readily removeable strip 44 as a temporary cover.

It is intended that the drip collector of this invention be put in place after urination or ejaculation and then disposed of prior to the next urination. Typically a user will carry a sufficient quantity to provide for the needs of the day. In order to keep the drip collectors clean until use, suitable packaging is provided.

Referring to FIG. 11, another drip collector 46 is shown with its associated package 48. Package 48 may be two sheets of cellophane or other sheet plastic sealed adjacent to the edges. Collector 46 is provided with ring 50 which aids in applying the drip collector as will now be described. Both drip collector 46 and ring 50 are formed of two similar joined halves. This form tends to naturally stay in a substantially flat condition as shown in FIG. 11. Each half of ring 50 is connected to the adjacent half of drip collector 46 by an adhesive strip 52. As shown in FIG. 14, the opposite edges of ring 50 are compressed causing both ring 50 and collector 46 to open. Ring 50 is moved over the glans penis, while bottom tab 54 is held. As ring 50 is moved further up the body of the penis, the adhesive strips 52 begin to peel off ring 50 and become positioned on the penis. This upward movement is continued, as shown in FIG. 13, until the strips 52 are completely separated from ring 50. Ring 50 is then torn apart or slipped back down off the penis and disposed of.

While the instant invention has been shown and described herein in what is conceived to be the most practical and preferred embodiment, it is recognized that departures may be made therefrom within the scope of the invention, which is therefore not to be limited to the details disclosed herein, but is to be afforded the full scope of the claims so as to embrace any and all equivalent apparatus and articles.

I claim:

1. A disposable post urination drip collector comprising:

a cap sized to cover substantially only the glans penis;
   said cap having a continuous inner layer of liquid permeable material, a coextensive outer layer of liquid impermeable material and an intermediate layer of liquid absorbent material;
   said inner and outer layers being sealably joined at their margins;
   said inner layer of said cap having an adhesive portion thereon structured to removably secure said cap upon the glans penis; and
   said adhesive portion having a removable cover thereon.

2. A post urination drip collector in accordance with claim 1 wherein:
   said adhesive portion is positioned to be adjacent to the neck of the penis on the upper surface of the glans penis.

3. A post urination drip collector in accordance with claim 1 wherein:
   said adhesive portion extends over the surface of said inner layer.

4. A post urination drip collector in accordance with claim 1 wherein:
   said cap is folded to a substantially semicircular configuration and is encased in a sealed package.

5. A post urination drip collector in accordance with claim 4 wherein:
   said package has an inner foil liner.

6. A post urination drip collector in accordance with claim 1 wherein:
   said cap has the configuration of the glans penis.

7. A post urination drip collector in accordance with claim 1 wherein:
   said cap has an edge defining an upper opening and at least one portion of said edge has an upwardly extending flap.

8. A post urination drip collector in accordance with claim 7 wherein:
   said cap has two, oppositely disposed upwardly extending flaps.

9. A post urination drip collector in accordance with claim 7 wherein:
   said flap has an adhesive portion with a removeable cover thereon.

10. A post urination drip collector in accordance with claim 1 wherein:

said cap has an edge defining an upper opening and said adhesive portion is a strip extending around said opening adjacent to said edge.

11. A post urination drip collector in accordance with claim 1 further including:
   a pair of strips having adhesive on one side;
   each of said strips having a portion secured by said adhesive to said outer layer in diametrically oppositely located positions;
   each of said strips having an additional portion of said adhesive removeably covered by a circumferentially extending ring;
   said ring having outwardly protruding seams, whereby said ring may be moved over the glans penis and along the body of the penis to uncover said additional portions of said adhesive while simultaneously positioning said strips.

12. A disposable post urination drip collector comprising:
   a cap sized to cover substantially only the glans penis;
   said cap having a continuous inner layer of liquid permeable material, a coextensive outer layer of liquid impermeable material and an intermediate layer of liquid absorbent material;
   said inner layer of said cap having an inner surface;
   said inner surface having an area having adhesive thereon located to be adjacent to the neck of the penis and on the upper side of the penis.

* * * * *